United States Patent [19]

Butler et al.

[11] Patent Number: 5,209,827
[45] Date of Patent: May 11, 1993

[54] PROCESS FOR THE PURIFICATION OF HYDROXYPIVALYL HYDROXYPIVALATE

[75] Inventors: Gerald E. Butler; Garrett C. Luce; Don L. Morris, all of Longview, Tex.

[73] Assignee: Eastman Kodak Company, Rochester, N.Y.

[21] Appl. No.: 743,639

[22] Filed: Aug. 12, 1991

Related U.S. Application Data

[63] Continuation-in-part of Ser. No. 604,277, Oct. 29, 1990, abandoned.

[51] Int. Cl.⁵ .......................... B01D 1/22; C07C 69/66
[52] U.S. Cl. ........................................ 203/72; 203/75; 203/77; 203/87; 203/94; 202/155; 560/189
[58] Field of Search ...................... 203/72, 89, 73, 74, 203/75, 77, 94, 98, 87; 560/189; 202/154, 155, 153, 186, 198

[56] References Cited

U.S. PATENT DOCUMENTS

| | | | |
|---|---|---|---|
| 1,676,675 | 7/1928 | Trumble | 202/198 |
| 2,520,870 | 8/1950 | Wood et al. | 203/72 |
| 3,096,274 | 7/1963 | Palmer | 202/198 |
| 3,379,624 | 4/1968 | Lindkvist | 202/236 |
| 3,476,656 | 11/1969 | Van Tassell et al. | 203/72 |
| 3,644,179 | 2/1972 | Knoer et al. | 203/72 |
| 3,696,005 | 10/1972 | Fuchs et al. | 560/189 |
| 3,697,387 | 10/1972 | Munch | 203/72 |
| 3,759,862 | 9/1973 | Fukui et al. | 560/185 |
| 3,892,634 | 7/1975 | Hajek et al. | 203/72 |
| 4,390,398 | 6/1983 | Coker et al. | 203/87 |
| 4,665,219 | 5/1987 | Merger et al. | 560/189 |

Primary Examiner—Wilbur Bascomb, Jr.
Attorney, Agent, or Firm—J. Frederick Thomsen; William P. Heath, Jr.

[57] ABSTRACT

Disclosed is a process for the recovery of purified hydroxypivalyl hydroxypivalate (HPHP) from a crude, HPHP containing material containing inorganic catalyst residues and low-boiling and high-boiling (with respect to the boiling point of HPHP) impurities. The purification process employs two distillation zones, a first distillation zone wherein inorganic and high-boiling impurities are removed and a second distillation zone wherein low- and high-boiling impurities are removed.

2 Claims, 1 Drawing Sheet

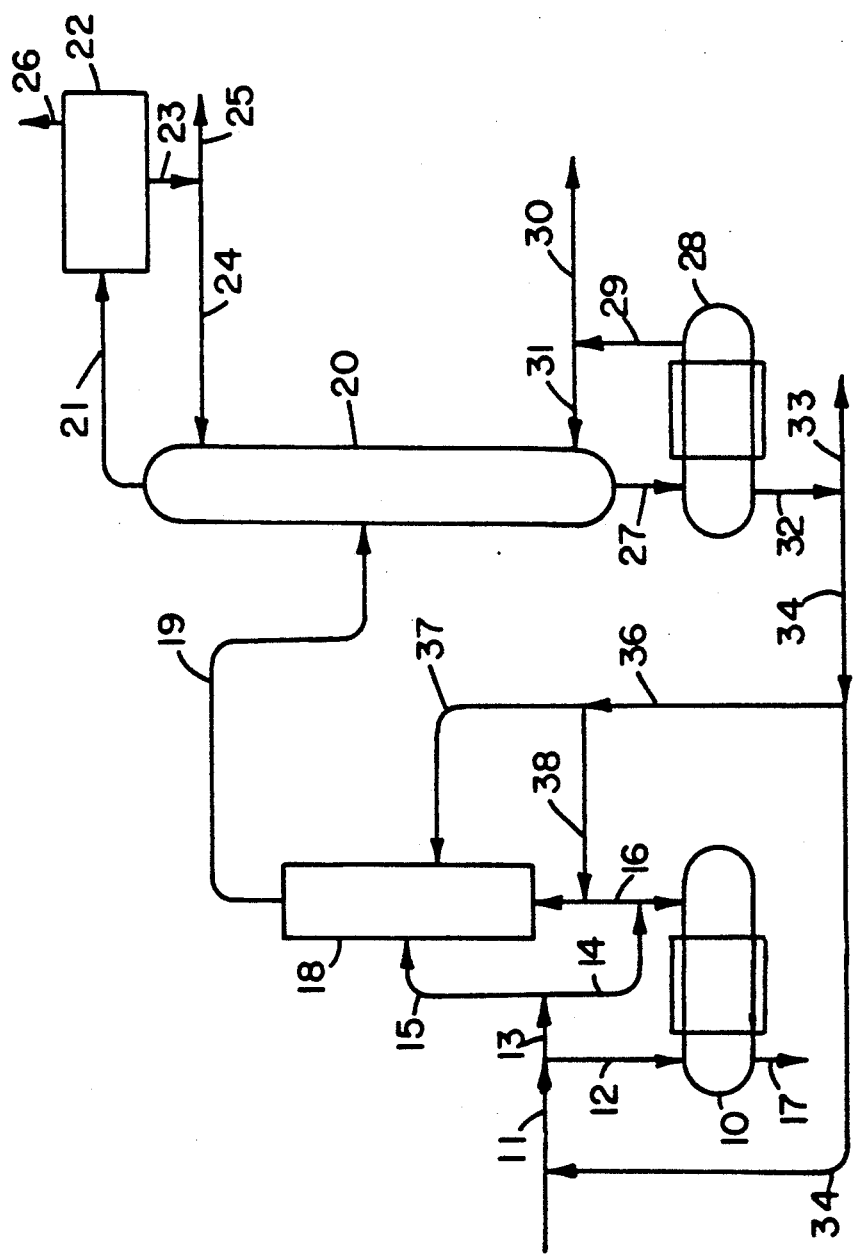
FIGURE

PROCESS FOR THE PURIFICATION OF HYDROXYPIVALYL HYDROXYPIVALATE

This application is a continuation in part of our co-pending application Ser. No. 07/604,277 filed Oct. 29, 1990, now abandoned.

This invention pertains to a process for the purification of hydroxypivalyl hydroxypivalate, i.e., the monoester of 2,2-dimethyl-1,3-propanediol and 2,2-dimethyl-3-hydroxypropanoic acid. More specifically, this invention pertains to the purification of a crude hydroxypivalyl hydroxypivalate which contains inorganic catalyst residues and low-boiling and high boiling components.

Hydroxypivalyl hydroxypivalate (HPHP) is useful in the production of lubricants, as described in U.S. Pat. No. 3,759,862, and especially in the manufacture of polyester resins used in the formulation of coating compositions. HPHP typically is produced by means of the Tischenko reaction wherein hydroxypivaldehyde is contacted with an alkaline catalyst. The crude HPHP thus obtained may contain up to 40 weight percent or more of impurities such as isobutyraldehyde, isobutanol, unreacted hydroxypivaldehyde, 2,2-dimethyl-1,3-pentanediol and 2,2-dimethyl-1,3-pentanediol monoisobutyrate as well as high-boiling components and inorganic catalyst residues. Some of the impurities may be introduced with the hydroxypivaldehyde reactant which is manufactured from isobutyraldehyde and formaldehyde.

HPHP, which has a boiling point of 160° C. at 8 torr, undergoes substantial decomposition when heated at temperatures in excess of 150° C. for periods of time exceeding 5 minutes, even at reduced pressures, and therefore is difficult to purify by normal vacuum distillation procedures. In addition to decreasing product yields, decomposition during the refining of crude HPHP results in the formation of highly colored compounds or components. For most end uses such as the preparation of polyester resins, it is important that HPHP have a color no greater than 10 APHA units measured by a Hunter colorimeter on a platinum-cobalt scale.

U.S. Pat. No. 3,641,118 discloses a process for the purification of HPHP which involves treating crude HPHP with an acidic ion exchange resin. According to this patent, purified HPHP is obtained by vacuum distillation at a boiling point of 152° C. at 10 torr. This patent does not disclose the means by which the vacuum distillation is carried out or the removal of low-boiling and high-boiling impurities.

Another process for the purification of HPHP is described in U.S. Pat. No. 3,696,005 wherein crude HPHP is admixed with sulfuric or a sulfonic acid and the resulting mixture is fed to a column at the distillation temperature under reduced pressure. According to this patent, pure ester is isolated as a sidestream and any light ends and solvent are taken overhead and the acid and impurities are discharged from the base of the column. The recovery of purified HPHP at 128°-130° C. at 2 torr is disclosed in the examples of the patent. In commercial operations, this purification method would generate a sulfur-containing, high-boiling stream which could pose disposal problems.

Chemical processors have utilized wiped film evaporators commercially for many years. Wiped film evaporators are available in both vertical and horizontal design. In each design a rotor wipes the heated surface of the evaporator to provide a thin layer of the heat-sensitive material. The rotor turns at speeds of from 100 to 1,000 revolutions per minute. The heat-sensitive material is mechanically pushed against the heated surface and wiped along with every turn of the rotor. This maximizes the heat transfer from the evaporator wall to the material. By maintaining a thin layer on the heated surface of the evaporator, the volume of material retained in the evaporator is kept to a minimum.

This type of equipment has found commercial acceptance for the distillation of highly heat-sensitive materials. U.S. Pat. No. 3,379,624 describes a chemical process which utilizes a vertical thin film evaporator to distill chemicals from salts. In the process described in U.S. Pat. No. 3,379,624, the salts are removed as a solid from the base of the evaporator, while the product is removed as a vapor from the top of the evaporator.

U.S. Pat. No. 3,476,656 discloses a process and an apparatus for the fractional distillation of styrene from sulfur, involving introducing styrene, sulfur, and a cutback oil into a fractionating column to obtain an overhead product of high purity styrene and a bottoms fraction containing the cut-back oil, sulfur, polymeric impurities, and minor amounts of styrene; passing the bottoms fraction to a wiped film evaporator to vaporize the minor amounts of styrene, which is preferably returned to the fractionating column, to obtain a bottoms fraction with reduced styrene content which is then passed to a separation zone, preferably a rotary drum filter, to separate solid sulfur from a liquid fraction, containing the cut-back oil and the polymeric impurities, which is subjected to a further fractionation, preferably in another wiped or agitated film evaporator. Both the purified sulfur and cut back oil may be recycled into the appropriate step(s) in the process.

U.S. Pat. No. 3,892,634 discloses a process for the separation of 2,4'- and 4,4'-methylenebis(phenyl isocyanate) from polymethylene polyphenyl polyisocyanates. The disclosed process involves subjecting a feed of polymethylene polyphenyl polyisocyanate to partial distillation in a first thin film evaporator to obtain an overhead fraction which is fractionated in a fractionator to yield another overhead fraction enriched in 2,4'-methylenebis(phenyl isocyanate). The bottoms fraction from the fractionator is subjected to a second partial distillation in a second thin film evaporator to obtain a minor overhead product, which is returned to the fractionator and an undistilled bottoms fraction which is subjected to a third partial distillation to remove the 4,4'-methylenebis(phenyl isocyanate) as an overhead product. The undistilled bottoms fraction from the first thin film evaporator contains polymethylene polyphenyl polyisocyanate.

We have discovered that substantially-pure HPHP, e.g., HPHP having a purity of 98% or greater and a color of 10 APHA units or less, may be recovered from crude HPHP containing inorganic catalyst residues and low-boiling and high-boiling (with respect to the boiling point of HPHP) components. The process of the present invention provides a means for the purification of crude HPHP using two distillation zones: a first distillation zone wherein inorganic and high-boiling impurities are removed and a second distillation zone wherein low- and high-boiling impurities are removed.

Our novel process therefore provides a process for the recovery of hydroxypivalyl hydroxypivalate, preferably having a purity of at least 98 weight percent and a color of 10 APHA units or less, from a crude mixture comprising hydroxypivalyl hydroxypivalate, low-boiling components, high-boiling components and inorganic catalyst residues, by the steps comprising:

(1) feeding the crude mixture to a first distillation zone comprising:
   (A) a first wiped film evaporator operated at about 150° to 250° C. and 1 to 100 torr; and
   (B) a partial condenser column operated at about 150° to 175° C. and 5 to 30 torr in which the temperature and pressure at the column head are about 1° to 5° C. and 1 to 5 torr lower than that existing at the base of the column;
   wherein (i) a liquid effluent comprising high boiling components and inorganic residues is removed from the first wiped film evaporator and (ii) a vapor effluent comprising hydroxypivalyl hydroxypivalate, low-boiling components and high-boiling components is removed from the partial condenser column;

(2) feeding the vapor effluent of step (1) to a second distillation zone comprising:
   (A) a low-boiler column operated at a column head temperature and pressure of about 90° to 120° C. and about 5 to 30 torr and a column base temperature and pressure of about 160° to 190° C. and about 10 to 30 torr;
   (B) condenser means; and
   (C) a second wiped film evaporator operated at about 160° to 190° C. and about 10 to 30 torr;
   wherein (i) a vapor effluent comprising low-boiling components is removed from the low boiler column and is fed to and condensed in the condenser means; (ii) a liquid effluent comprising hydroxypivalyl hydroxypivalate and high-boiling components is removed from the low boiler column and fed to the second wiped film evaporator; and (iii) a liquid effluent comprising high-boiling components is removed from the second wiped film evaporator; and (3) recovering a vapor effluent comprising purified hydroxypivalyl hydroxypivalate from the second wiped film evaporator.

The accompanying FIGURE schematically depicts one embodiment for carrying out the purification process provided by the present invention. The first distillation zone of the refining system comprises wiped film evaporator 10 and partial condenser column 18. The second low-boiler removal section comprises low-boiler column 20, condenser 22 and wiped film evaporator 28. All of the heat required for both distillation zones is provided by superheat in the feed and the two wiped film evaporators.

The crude HPHP is fed via conduit 11 to the first distillation zone of the purification apparatus at any of a plurality of points as depicted in the FIGURE. Thus, the crude HPHP may be fed directly to the first wiped film evaporator via conduits 11 and 12. Alternatively, some or all of the crude HPHP may be fed to partial condenser column 18 via conduits 11, 13, and 15, or to wiped film evaporator, vapor take-off conduit 16 via conduits 11, 13 and 14 from where some or all of the crude HPHP, depending on the mode of operation, descends via line 16 to wiped film evaporator 10. It is apparent that the base of partial condenser 18 may be connected directly to the wiped film evaporator.

A substantial portion of the HPHP-containing crude mixture is vaporized in wiped film evaporator 10 at a temperature of about 150° to 250° C. and a pressure of about 1 to 100 torr, preferably at a temperature of about 150° to 200° C. and a pressure of about 5 to 50 torr. The combination of feed rate of crude HPHP to evaporator 10 and the temperature and pressure maintained therein provides a residence time of the HPHP component of the feed of about 5 to 120 seconds, preferably about 10 to 60 seconds.

The inorganic salts and a portion, e.g. 30 to 70 weight percent, of the high-boiler impurities of the crude HPHP are removed from the purification system as a liquid through conduit 17. The remainder of the crude mixture is vaporized by means of Evaporator I and fed via conduit 16 to the base of partial condenser column 18 which includes heat exchanger means for condensing a portion of the vapor. The partial condenser column may include heat exchanger means which may be positioned within the column near the top thereof or may be located exterior to the column wherein a portion of the vapor feed to the column is condensed and returned to the column.

The partial condenser column is operated at a pressure of about 5 to 30 torr and a temperature of about 150° to 175° C. in which the temperature and pressure at the column head are about 1° to 5° C. and 1 to 5 torr lower than the temperature and pressure existing at the base of the column. The column typically contains a packing material or trays to provide intimate liquid-vapor contact. The purpose of the partial condenser means is to ensure complete removal of the inorganic salts and to maximize removal of the high-boiler impurities through line 17.

The vapor effluent from partial condenser means 18 is fed through conduit 19 to the second distillation zone of the purification system at the mid-section of low boiler column 20 which contains packing material above and below the feed point. The column 20 feed contains a significant amount, e.g., 20 to 40 weight percent of low-boiler impurities as well as some high-boiler components. Column 20 is operated at a column head temperature and pressure of about 90° to 120° C. and about 5 to 30 torr and a column base temperature and pressure of about 160° to 190° C. and about 10 to 30 torr with the feed temperature being approximately equal to that of the column head temperature of the partial condenser column.

The low boiler components of the crude HPHP fed to column 20 are removed via conduit 21 and fed to primary condenser means 22 comprising 1 or more condensers for the recovery of the low-boiler impurities. A substantial portion, e.g., 50 to 75 weight percent, of the condensed low-boilers are recycled by means of conduits 23 and 24 to column 20 at or near its top to maximize the condensation of HPHP in column 20. The remainder of the condensed low-boilers are removed from the purification system via lines 23 and 25 and are either processed further or incinerated. Uncondensible components are removed from the primary condenser means via conduit 26.

The liquid material which is removed (underflowed) from low boiler column 20 to wiped film evaporator 28 via conduit 27 consists essentially of HPHP and a minor amount, e.g., up to about 3 weight percent, of high-boiler components including highly colored components. Wiped film evaporator 28 serves as the base heater for column 20 and thus is operated at a temperature and pressure of about 160° to 190° C. and about 10 to 30 torr. The purpose of wiped film evaporator 28 is to further reduce the high boiler compounds present in the otherwise pure HPHP and, especially, to remove highly colored components of the high boiler compounds.

Most of the feed to wiped film evaporator 28, typically at least 90 weight percent, is vaporized and the vapors are removed through conduit 29. Purified HPHP, normally having a purity in excess of 98%, is recovered from the refining system via conduits 29 and 30. About 50 to 80 weight percent of the vapor stream of conduit 28 normally is recycled through conduit 31 to the lower section of column 20 to provide heat for the operation of the low boiler column and to enhance the removal of the high boiling components.

A liquid effluent comprising HPHP and high boilers is removed from wiped film evaporator 28 by conduit 32 and may be purged from the system through line 33. Preferably, the liquid effluent is returned via conduits 32 and 34 to the first distillation zone of the refining system at any of several points as depicted by conduits 35, 36, 37 and 38 in the FIGURE. This preferred handling of the effluent from wiped film evaporator 28 permits recovery of the HPHP present in the effluent and the collection of the high boiling components from purge line 17.

The purification process described herein has several significant advantages over typical organic chemical distillation systems. First, the combination of a wiped film evaporator and a partial condenser column to remove inorganic and high-boiling impurities provides a means to continuously distill a very heat-sensitive compound at a relatively high temperature. This permits recovery of at least 95 percent of the desirable product overhead with minimal decomposition in the base heater. With a standard flash column using a tubular base heater the yield loss to high-boiling impurities is about 10 percent. Taking the vapor from the partial condenser column directly to the low boiler column provides advantages in energy savings and in capital equipment. The vapor does not have to be cooled, saving cooling costs, and the feed to the column does not have to be vaporized, saving heating costs. The partial condenser column and the low boiler column share a common vacuum system, representing a significant capital cost savings. The use of a second wiped film evaporator as the base heater for the low boiler column makes it possible to distill the heat sensitive HPHP without fear of decomposition in the base heater of the column. The ultimate yield of product from crude mixture is improved by about 15 percent by using the dual wiped film evaporator scheme. The capital investment in equipment is also lowered by about 5 percent. Of even greater significance is the fact that with the present method it is possible to produce a superior quality product as compared to that obtained by conventional methods. Thus, the product obtained by the present method is 98.4 percent HPHP, while the product obtained by conventional methods is only 97.5 percent HPHP.

A preferred embodiment of our process comprises:
(1) feeding the crude mixture to a first distillation zone comprising:
  (A) a first wiped film evaporator operated at about 150° to 200° C. and 10 to 30 torr; and
  (B) a partial condenser column operated at about 150° to 175° C. and 5 to 30 torr in which the temperature and pressure at the column head are about 1° to 5° C. and 1 to 5 torr lower than the temperature and pressure existing at the base of the column;
  wherein (i) a liquid effluent comprising high boiling components and inorganic residues is removed from the first wiped film evaporator and (ii) a vapor effluent comprising hydroxypivalyl hydroxypivalate, low-boiling components and high-boiling components is removed from the partial condenser column;
(2) feeding the vapor effluent of step (1) to a second distillation zone comprising:
  (A) a low-boiler column operated at a column head temperature and pressure of about 90° to 120° C. and about 5 to 30 torr and a column base temperature and pressure of about 160° to 190° C. and about 10 to 30 torr;
  (B) condenser means; and
  (C) a second wiped film evaporator operated at about 160° to 190° C. and about 10 to 30 torr;
  wherein (i) a vapor effluent comprising low-boiling components is removed from the low boiler column and is fed to and condensed in the condenser means and about 50 to 75 weight percent of the condensed low boiling components is recycled to the upper section of the low boiler column; (ii) a liquid effluent comprising hydroxypivalyl hydroxypivalate and high-boiling components is removed from the low boiler column and fed to the second wiped film evaporator; (iii) a liquid effluent comprising high-boiling components is removed from the second wiped film evaporator; and (iv) a vapor effluent is removed from the second wiped film evaporator and recycled to the lower section of the low boiler column; and
(3) recovering a vapor effluent comprising purified hydroxypivalyl hydroxypivalate from the second wiped film evaporator.

The operation of our novel process is further illustrated by the following example wherein all parts and percentages given are by weight. The crude HPHP used is produced by the catalytic dimerization of hydroxypivaldehyde in the presence of a magnesium or calcium compound such as magnesium carbonate or calcium hydroxide and contains 66.3% HPHP, 3.8% high-boiling impurities, 0.02% catalyst residues in the form of metal salts and 29.9% of low-boiling impurities comprised of water, isobutyraldehyde, isobutanol, hydroxypivaldehyde, neopentyl glycol (NPG; 2,2-dimethyl-1,3 -pentanediol), NPG isobutyrate and NPG hydroxypivaldehyde acetal.

Crude HPHP is fed to the base of partial condenser column 15 at the rate of 722 parts per hour. In the apparatus used, the base of the partial condenser column is affixed on and to the upper surface of a horizontal wiped film evaporator. Wiped film evaporator 10 is operated at a temperature of about 167° C. and a pressure of 17 torr and partial condenser is maintained at a base temperature and pressure of 167° C. and 17 torr and a column top temperature and pressure of 162° C. and 15 torr. Under these conditions, the first distillation zone produces (i) a liquid effluent containing the alkaline catalyst residues and about 39% high boilers which is removed from wiped film evaporator 10 through conduit 17 at the rate of 44.7 parts per hour and (ii) a vapor effluent containing HPHP and low and high boiling components which is removed from the top of partial condenser 18 by conduit 19 at the rate of 677.6 parts per hour.

The vapor effluent is fed by conduit 19 to the mid-section of low-boiler column 20 which is maintained at a base temperature and pressure of 172° C. and 16 torr and a top temperature and pressure of 104° C. and 12 torr. Wiped film evaporator 28 of the second distillation zone is operated at a temperature of approximately 172° C. and 16 torr. A vapor effluent comprising low-boiling components is removed from low boiler column 20 and transported by line 21 to condenser means 22 at a rate of 891.2 parts per hour. Condensed liquids from condenser means 22 are recycled via lines 23 and 24 to the upper section of low boiler column 20 at a rate of 673.8 parts per hour. The remainder of the condensed liquids is removed from the purification system by conduits 23 and 25.

A liquid effluent comprising HPHP and high boiling components is removed from the base of the low boiler column and fed via conduit 27 to wiped film evaporator 28 at a rate of 1081.6 parts per hour. A second liquid effluent comprising HPHP and high boilers is removed at a rate of 45.9 parts per hour from wiped film evaporator 28 through conduit 32 and recycled and fed to the first distillation zone with the crude HPHP.

A vapor effluent is removed from wiped film evaporator 28 through line 29 at a rate of 1035.7 parts per hour and a portion (416.7 parts per hour) of this HPHP product stream is removed from the purification system by conduit 30 and condensed. The HPHP thus obtained has a purity of 98.3% and a color of 3 APHA units. To provide heat to the low boiler column and enhance removal of high boilers, a portion of the vapor stream of line 29 is recycled to the base of low boiler column 20 via line 31.

Obviously, numerous modifications and variations of the present invention are possible in light of the above teachings. It is therefore to be understood that, within the scope of the appended claims, the invention may be practiced otherwise than as specifically described herein.

We claim:

1. Process for the recovery of hydroxypivalyl hydroxypivalate from a crude mixture comprising hydroxypivalyl hydroxypivalate, low-boiling components, high-boiling components and inorganic catalyst residues, by the steps comprising:
   (1) feeding the crude mixture to a first distillation zone comprising:
      (A) a first wiped film evaporator operated at about 150° to 250° C. and 1 to 100 torr; and
      (B) a partial condenser column operated at about 150° to 175° C. and 5 to 30 torr in which the temperature and pressure at the column head are about 1° to 5° C. and 1 to 5 torr lower than that existing at the base of the column;
      wherein (i) a liquid effluent comprising high boiling components and inorganic residues is removed from the first wiped film evaporator and (ii) a vapor effluent comprising hydroxypivalyl hydroxypivalate, low-boiling components and high-boiling components is removed from the partial condenser column;
   (2) feeding the vapor effluent of step (1) to a second distillation zone comprising:
      (A) a low-boiler column operated at a column head temperature and pressure of about 90° to 120° C. and about 5 to 30 torr and a column base temperature and pressure of about 160° to 190° C. and about 10 to 30 torr;
      (B) condenser means; and
      C) a second wiped film evaporator operated at about 160° to 190° C. and about 10 to 30 torr;
      wherein (i) a vapor effluent comprising low-boiling components is removed from the low boiler column and is fed to and condensed in the condenser means; (ii) a liquid effluent comprising hydroxypivalyl hydroxypivalate and high-boiling components is removed from the low boiler column and fed to the second wiped film evaporator; and (iii) a liquid effluent comprising high-boiling components is removed from the second wiped film evaporator; and
   (3) recovering a vapor effluent comprising purified hydroxypivalyl hydroxypivalate from the second wiped film evaporator.

2. Process for the recovery of hydroxypivalyl hydroxypivalate having a purity of at least 98 weight percent and a color of 10 APHA units or less from a crude mixture comprising hydroxypivalyl hydroxypivalate, low-boiling components, high-boiling components and inorganic catalyst residues, by the steps comprising:
   (1) feeding the crude mixture to a first distillation zone comprising:
      (A) a first wiped film evaporator operated at about 150° to 200° C. and 10 to 30 torr; and
      (B) a partial condenser column operated at about 150° to 175° C. and 5 to 30 torr in which the temperature and pressure at the column head are about 1° to 5° C. and 1 to 5 torr lower than the temperature and pressure existing at the base of the column;
      wherein (i) a liquid effluent comprising high boiling components and inorganic residues is removed from the first wiped film evaporator and (ii) a vapor effluent comprising hydroxypivalyl hydroxypivalate, low-boiling components and high-boiling components is removed from the partial condenser column;
   (2) feeding the vapor effluent of step (1) to a second distillation zone comprising:
      (A) a low-boiler column operated at a column head temperature and pressure of about 90° to 120° C. and about 5 to 30 torr and a column base temperature and pressure of about 160° to 190° C. and about 10 to 30 torr;
      (B) condenser means; and
      (C) a second wiped film evaporator operated at about 160° to 190° C. and about 10 to 30 torr;
      wherein (i) a vapor effluent comprising low-boiling components is removed from the low boiler column and is fed to and condensed in the condenser means and about 50 to 75 weight percent of the condensed low boiling components is recycled to the upper section of the low boiler column; (ii) a liquid effluent comprising hydroxypivalyl hydroxypivalate and high-boiling components is removed from the low boiler column and fed to the second wiped film evaporator; (iii) a liquid effluent comprising high-boiling components is removed from the second wiped film evaporator; and (iv) a vapor effluent is removed from the second wiped film evaporator and recycled to the lower section of the low boiler column; and
   (3) recovering a vapor effluent comprising purified hydroxypivalyl hydroxypivalate from the second wiped film evaporator.

* * * * *